United States Patent
Busby et al.

(10) Patent No.: US 6,575,011 B1
(45) Date of Patent: Jun. 10, 2003

(54) BLADE TIP CLEARANCE PROBE AND METHOD FOR MEASURING BLADE TIP CLEARANCE

(75) Inventors: R. L. Busby, Lake Park, FL (US); Richard M. Muny, Fisherville, KY (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 184 days.

(21) Appl. No.: 09/837,810

(22) Filed: Apr. 19, 2001

(51) Int. Cl.[7] .................................................. G01N 3/56
(52) U.S. Cl. .................................................... 73/7
(58) Field of Search ........................... 73/118.1–117.3, 73/7; 324/662; 415/171; 250/561

(56) References Cited

U.S. PATENT DOCUMENTS 3,932,941 A * 1/1976 Ormsby ........................... 73/7
5,017,796 A   5/1991 Makita
5,497,101 A   3/1996 Fillion
5,739,524 A   4/1998 Fally
5,760,593 A   6/1998 Lawrence et al.

* cited by examiner

Primary Examiner—Helen Kwok
Assistant Examiner—Tamiko Bellamy
(74) Attorney, Agent, or Firm—Mark O. Glut

(57) ABSTRACT

A blade tip clearance probe including a rub probe support removably attachable to a probe boss attachable to a fan case; a rub probe removably attachable to the rub probe support, the rub probe is composed of soft composite material, the rub probe support is able to receive the rub probe such that the rub probe can be adjusted to contact a blade tip; and an anti rotational lock being able to lock the rub probe into place in the rub probe support and being able to prevent rub prove movement. A method for measuring blade tip clearance including: fastening a rub probe support to a probe boss attached to a fan case; threading a rub probe into the rub probe support until the rub probe contacts a blade tip in the fan case; backing the rub probe off a specified turn angle; operating an engine attached to the blade tip; and measuring the probe wear.

6 Claims, 2 Drawing Sheets

BLADE TIP CLEARANCE PROBE AND METHOD FOR MEASURING BLADE TIP CLEARANCE

STATEMENT OF GOVERNMENT INTEREST

The invention described herein may be manufactured and used by or for the Government of the United States of America for governmental purposes without payment of any royalties thereon or therefor. This invention was invented under contract number N00019-97-C-0050 with United Technologies Pratt & Whitney.

BACKGROUND

The present invention relates to a blade tip clearance probe and a method for measuring blade tip clearance. More specifically, but without limitation, the present invention relates to a blade tip clearance probe that measures the gap between a blade tip and blade housing (or fan case) and a method for measuring blade tip clearance in an engine.

Gas turbine engines, steam turbines, aircraft engines, jet engines and other axial flow turbomachinery are typically designed to minimize the radial gap between a blade tip and a blade housing or fan case. Gaps between blade tips and fan cases (commonly referred to as blade tip gap) reduce efficiency by allowing gas or air to leak into the preceding stage of engine operation. The blade tip gap is a function of engine speed and temperature, and it changes during engine operation. High operating rotational speeds cause radial elastic growth in rotating hardware (i.e. blades), resulting in radial blade tip growth. High temperatures cause thermal expansion in the case and in the rotating hardware. A nondestructive inspection method of determining this gap at operating conditions is needed.

A thin metal rod can be used as a probe to measure the blade tip gap. The rod is inserted into an axially drilled bolt and fastened into place. The resulting assembly is then inserted into a mount plate attached to the fan case and the engine is operated for a specified time period. The amount of wear on the rod is recorded to determine the change in blade tip gap. The rods often bend or break which negates any data that was recorded. In addition, metal liberated from the rod, either as pieces or as powder can cause damage to the engine. Making these rods/probes is difficult and time consuming. Each probe must be custom made using a measurement of distance from the fan case boss to the blade tip. This introduces many errors such as measurement, data recording, and machining. Often the probes are made too short or too long. Short probes do not rub the blade tip, while long probes bend or break.

Engine testing, specifically aircraft engine testing, is very expensive and time schedules for testing are very tight. Performing multiple tests is often not an option. Many engine tests utilize electrical and/or laser equipment that is difficult to use and expensive to use and maintain.

For the foregoing reasons, there is a need for a new blade tip clearance probe and a method for measuring blade tip clearance. Information relevant to attempts to address these problems can be found in U.S. Pat. Nos. 5,017,796, 5,497, 101, 5,760,593; and 5,739,524 (None of these patents are admitted to be prior art with respect to the present invention.) However, each of these references suffers from one of the above listed disadvantages.

SUMMARY

The present invention is directed to a blade tip clearance probe and a method for measuring blade tip clearance that satisfies the needs listed above and below.

The present invention is directed to a blade tip clearance probe, which includes a rub probe support, a rub probe and an anti rotational lock. The rub probe support can be removably attached to a probe boss, which can be removably attached to a fan case or blade housing. The rub probe can be removably attached to the rub probe support. The rub probe is composed of soft composite material and is able to be threaded into the rub probe support. The anti rotational lock is able to lock the rub probe into place in the rub probe support and is able to prevent rub prove movement.

The present invention is also directed to a method for measuring blade tip clearance, which includes fastening a rub probe support to a probe boss attached to a fan case; threading a rub probe into the rub probe support until the rub probe contacts a blade tip in the fan case; backing the rub probe off a specified turn angle; operating an engine attached to the blade tip; and measuring wear on the rub probe.

It is an object of the invention to provide a blade tip clearance probe that is simple and inexpensive to manufacture, as well as easy to use. It is also an object of the invention to provide a blade tip clearance probe that does not need to be custom made. It is a further object of the invention to provide a blade tip clearance probe that can be produced in bulk and thus be more economical.

It is also an object of the invention to provide a blade tip clearance probe and method for measuring blade tip clearance that is non-destructive and safe. It is also an object of the present invention to provide a blade tip clearance probe and a method for measuring blade tip clearance that does not cause damage to the blade tips or the fan case. Since the rub probe is manufactured from soft composite material, it will not cause damage to the blade tips, the fan case or any other parts of the engine. The powder that is liberated from the rub probe during operation poses no damage risk to the engine.

It is also an object of the invention to provide a blade tip clearance probe and method for measuring blade tip clearance that is reliable and does not cause tolerances (an allowable variation in dimensions) to accumulate.

DRAWINGS

These and other features, aspects and advantages of the present invention will become better understood with reference to the following description and appended claims and accompanying drawings wherein:

DESCRIPTION

Figure 1:
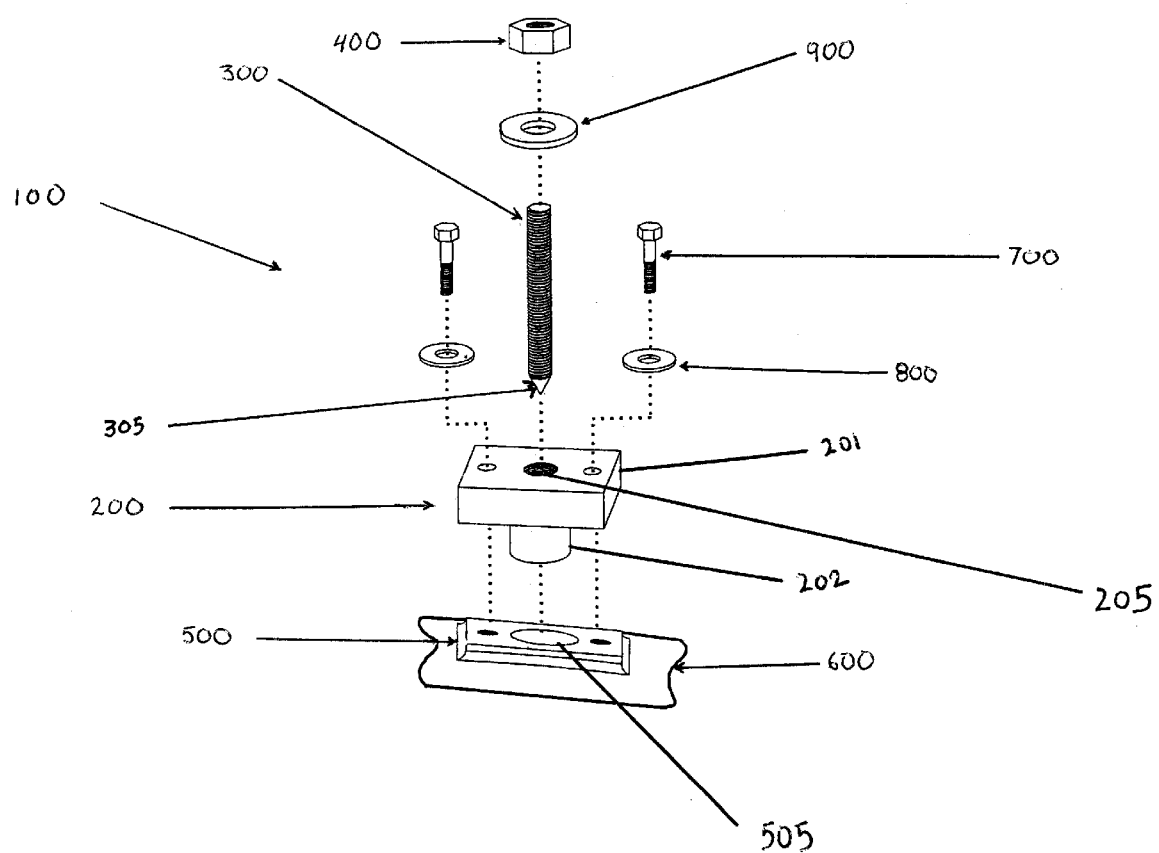
FIG. 1 is exploded perspective view of the blade tip clearance probe.
Figure 2:
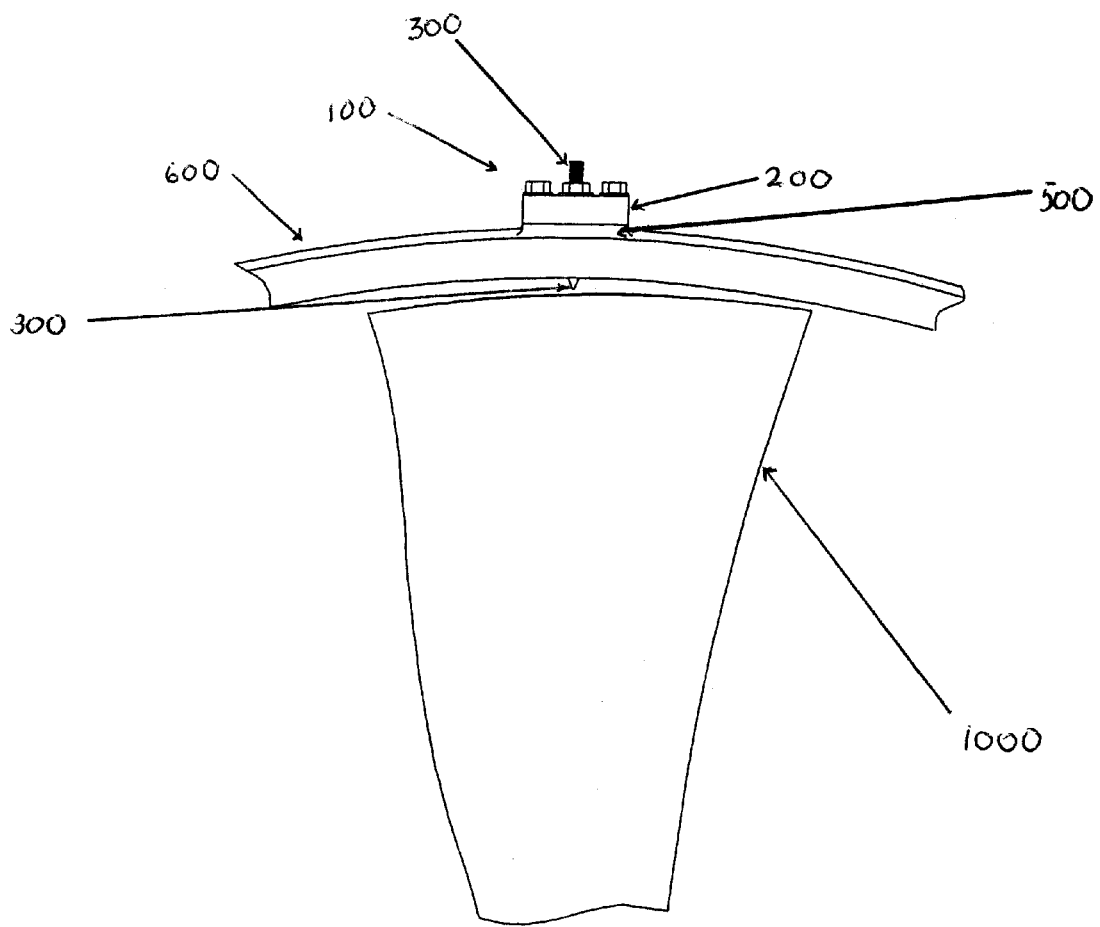
FIG. 2 is a side cross sectional view of the blade tip clearance probe attached to a fan case, and in operation.

The preferred embodiment of the present invention is illustrated by way of example in FIGS. 1 and 2. As shown in FIGS. 1 and 2, a blade tip clearance probe 100 includes a rub probe support 200, a rub probe 300 and an anti rotational lock 400. The rub probe support 200 may be removably attached to a probe boss 500, which may be removably attached to a fan case 600. The rub probe 300 may be removably attached to the rub probe support 200.

A probe boss 500 is typically a plate, member, platform, mounting, or the like, that is attached to a fan case 600 or blade housing of an engine. A fan case 600 or blade housing is a cover, container, frame, casing, box, shell, chamber, canister, housing, or the like, that contains a fan or blades required for engine operation. Typically there is a plurality of blade tips 1000 disposed within a fan case 600. In the preferred embodiment, the rub probe support 200 is removably attached to the probe boss 500. The probe boss 500 acts as a support, brace, underpinning, buttress, prop, or the like, for the rub probe support 200. The probe boss 500 may be attached to the fan case 600 via a fastener, screw, nail, anchor, dowel, weld, bolt, coupling, latch, lug, lock, pin, rivet, any type of connector or fastener, or the like. In some instances the probe boss 500 may be permanently attached or fixed to the fan case 600. The rub probe support 200 may be attached to the probe boss 500 utilizing similar type fasteners. As shown in FIG. 1, in the preferred embodiment, rub probe support mounting bolts 700 along with rub probe support mounting bolt washers 800 are used to attach the rub probe support 200 to the probe boss 500. In another embodiment, one fastener or one set of fasteners may be used to attach the rub probe support 200 to the boss probe 500 and the boss probe 500 to the fan case 600. The rub probe support 200 can be attached to the probe boss 500 and fan case 600 in a variety of ways. They can be mounted using magnets, glue, screws, nails, staples, hooks, clamps, lugs, pins, rivets, couplings, any type of fastener, any type of connector, an attachment mechanism or system, or the like.

In the preferred embodiment the probe boss 500 has a probe boss passage 505 which corresponds to an opening in the fan case 600. The opening in the fan case 600 allows communication with the blade tip(s) 1000. The rub probe support 200 receives the rub probe 300 such that the rub probe 300 is able to contact and/or physically communicate with a blade tip 1000 or blade tips. In the preferred embodiment, the rub probe support 200 has a housing passage 205. The housing passage 205 may be cylindrical in shape. The housing passage 205 is aligned with the probe boss passage 505 and the opening in the fan case 600 such that the rub probe 300 is able to be adjusted to contact the blade tip 1000. As shown in FIG. 1, the rub probe support 200 may have an upper portion 201 that is substantially rectangular in shape and a lower portion 202 that is substantially cylindrical in shape. The housing passage 205 passes through both the upper portion 201 and lower portion 202 of the rub probe support 200. In operation, the probe boss passage 505 may receive the lower portion 202 of the rub probe support 200, the housing passage 205 receives the rub probe 300 and the rub probe 300 is adjusted to pass through the housing passage 205, through the probe boss passage 505, through the opening in the fan case 600 and contact the blade tip 1000 disposed within the fan case 600. In the preferred embodiment the rub probe 300, the housing passage 205 may be axially aligned. The axis of a cylinder is typically the center of the cross sectional area (typically a circle in the case of a cylinder). To be axially aligned the axes of the objects are aligned such that it appears that all the axes continue as one straight axis.

The rub probe 300 can be manufactured from rubber, a petroleum-based product, textiles, any soft composite material, or the like. The fiber, matrix of the composite helps the rub probe 300 resist fracture. The rub probe 300 can also be manufactured from phenolic. Phenolic is a polymer comprising of phenolic resin. The key raw material in phenolic resins is phenol. Phenols are aromatic alcohols; they have a benzene like aromatic ring bonded to a hydroxyl group. The general structure of a phenol is ArOH, with Ar symbolizing an aromatic ring. The preferred embodiment of the rub probe 300 is manufactured from a paper-based laminate with a phenolic resin. The paper-based laminate can be Garolite(™) Grade XX. Paper-based laminate with a phenolic resin is a uniformly dense and solid material formed from layers of paper, impregnated with a synthetic resin under intense pressure and heat. The preferred paper based laminate with a phenolic resin of the rub probe 300 has a specific gravity in the range of about 1.10 to about 1.40. The material can also be non-volatile as to flash ignition temperature. The preferred material also may have a percent volatile by volume in the range of about 0.3% to about 1.0%.

As shown in FIG. 1, the rub probe 300 can have a cylindrical portion, which can be similar to a rod. The rub probe 300 can also have a conic tip 305. A rub probe 300 manufactured from the preferred material can be cut to a specified size and can be machined to obtain the conic tip. The preferred diameter of the cylinder portion of rub probe 300 is ¼ of an inch. The rub probe 300 can be threaded into the rub probe support 200 via the housing passage 205. The rub probe 300 and rub probe support 200 can have prefabricated corresponding threads. As shown in FIG. 1, in the preferred embodiment, the entire outer diameter of the cylinder portion of the rub probe 300 is threaded, and the housing passage 205 of the rub probe support 205 is also threaded and is of a size a corresponding to the diameter of the cylinder portion of the rub probe 300. This allows the rub probe 300 to be torqued and act in a manner similar to a screw.

The anti rotational lock 400 is able to lock the rub probe 300 into place in the rub probe support 200 and prevent any rub probe 300 movement. As shown in FIG. 1, the anti rotational lock 400 can be an anti rotational nut with an anti rotational washer 900. Any type of lock, mechanism, device, system, matrix, holder, configuration, means or apparatus that prevents rub probe 300 movement may be used.

The method for measuring blade tip clearance includes attaching a rub probe support 200 to a fan case 600. A probe boss 500 can be used as an intermediary attachment. As shown in FIG. 2, the rub probe 300 is threaded into the rub probe support 200 until the rub probe 300 contacts a blade tip 1000 in the fan case 600. The rub probe 300 must then be measured. This can be done by removal of the rub probe support 200 and/or probe assembly, then directly measuring the rub probe 300 in the rub probe support 200 after the length is initially set (prior to backing off the specified dimension). One may also measure the dimension from the probe boss 500 face to the blade tip 1000 prior to housing installation on the probe boss 500. The rub probe 300 is then backed off a specified turn angle. The preferred distance is 0.005 inches to ensure aerospace tolerances. The rub probe 300 is then locked into place with an anti rotational lock 400. The anti rotational lock 400 can be an anti rotational nut and anti rotational washer 900. When torqued, the anti rotational lock 400 prevents rub probe 300 movement by forcing the rub probe threads into the housing passage 205 threads. The retention force caused by friction between the threaded surfaces is greater than the vibratory forces working to loosen the rub probe 300. Reduction in the gap between the blade tip 1000 and the fan case 600 during operation causes the blade tip 1000 to contact and wear the rub probe 300. Once the test is completed, the rub probe support 200 and rub probe 300 are removed as an assembly from the fan case. The rub probe 300 length is measured from the inboard rub probe support 200 to the rub probe 300 tip. This dimension along with the prior dimension can be used to calculate fan blade growth due to rotation forces and thermal expansion. This value is used to calculate the blade tip clearance at the tested engine operating point.

Although the present invention has been described in considerable detail with reference to certain preferred versions thereof, other versions are possible. Therefore, the spirit and scope of the appended claims should not be limited to the description of the preferred versions contained herein.

Any element in a claim that does not explicitly state "means for" performing a specified function, or "step for" performing a specific function, is not to be interpreted as a "means" or "step" clause as specified in 35 U.S.C. 112 paragraph 6. In particular, the use of "step of" in the claims herein is not intended to invoke the provisions of 34 U.S.C. 112 paragraph 6.

What is claimed is:

1. A blade tip clearance probe, the blade tip clearance probe utilizing a probe boss attached to a fan case with a blade tip disposed within said fan case, the blade tip clearance probe comprising:
    a.) a rub probe support removably attached to said probe boss;
    b.) a rub probe removably attached to the rub probe support, the rub probe being composed of soft composite material, the rub probe support being able to receive the rub probe such that the rub probe being able to be adjusted to contact said blade tip, the rub probe manufactured from a paper-based laminate with a phenolic resin; and
    c.) an anti rotational lock to prevent rub probe movement, the anti rotational lock being able to lock the rub probe into place in the rub probe support.

2. The blade tip clearance probe of claim 1, wherein the paper based laminate with a phenolic resin has a specific gravity in the range of 1.10 to 1.40.

3. The blade tip clearance probe of claim 2, wherein the rub probe has a conic tip.

4. The blade tip clearance probe of claim 3, wherein the rub probe and rub probe support having corresponding threads.

5. The blade tip clearance probe of claim 4, wherein the rub probe support comprises of a housing passage, an upper portion, and a lower portion, the upper portion being rectangular in shape, the lower portion being cylindrical in shape, the rub probe being cylindrical in shape, the housing passage passing through the upper portion and the lower portion, the housing passage accepting the rub probe, the rub probe and housing passage being axially aligned.

6. A method for measuring blade tip clearance, comprising:
    a.) attaching a rub probe support to a probe boss attached to a fan case;
    b.) threading a rub probe into the rub probe support until the rub probe contacts a blade tip in the fan case, the rub probe manufactured from a paper based laminate with a phenolic resin, the phenolic resin having a specific gravity in a range of about 1.10 to about 1.40;
    c.) backing the rub probe off about 0.005 inches;
    d.) operating an engine attached to the blade tip; and
    e.) measuring wear on the rub probe.

* * * * *

UNITED STATES PATENT AND TRADEMARK OFFICE
CERTIFICATE OF CORRECTION

PATENT NO.     : 6,575,011 B1
DATED          : June 10, 2003
INVENTOR(S)    : R.L. Busby and Richard M. Muny It is certified that error appears in the above-identified patent and that said Letters Patent is hereby corrected as shown below:

Column 4,
Line 20, delete "205" (in the 2$^{nd}$ instance) and insert -- 200 -- therefor.
Line 21, delete "a" (in the 2$^{nd}$ instance).

Signed and Sealed this

Second Day of September, 2003

JAMES E. ROGAN
*Director of the United States Patent and Trademark Office*